United States Patent
Watanabe

(10) Patent No.: US 12,202,791 B2
(45) Date of Patent: Jan. 21, 2025

(54) METHOD FOR PRODUCING 3,5-DIHYDROXY-4-METHOXYBENZYL ALCOHOL FROM BIVALVE

(71) Applicant: WATANABE OYSTER LABORATORY, CO., LTD., Tokyo (JP)

(72) Inventor: Mitsugu Watanabe, Tokyo (JP)

(73) Assignee: WATANABE OYSTER LABORATORY CO., LTD., Tokyo (JP)

( * ) Notice: Subject to any disclaimer, the term of this patent is extended or adjusted under 35 U.S.C. 154(b) by 492 days.

(21) Appl. No.: 17/311,020

(22) PCT Filed: Sep. 27, 2019

(86) PCT No.: PCT/JP2019/038301
§ 371 (c)(1),
(2) Date: Jun. 16, 2021

(87) PCT Pub. No.: WO2020/129349
PCT Pub. Date: Jun. 25, 2020

(65) Prior Publication Data
US 2022/0017443 A1 Jan. 20, 2022

(30) Foreign Application Priority Data
Dec. 20, 2018 (JP) .................. 2018-238474

(51) Int. Cl.
C07C 41/34 (2006.01)
B01D 11/04 (2006.01)
C07C 41/36 (2006.01)

(52) U.S. Cl.
CPC .......... *C07C 41/36* (2013.01); *B01D 11/0488* (2013.01); *B01D 11/0492* (2013.01); *C07C 41/34* (2013.01)

(58) Field of Classification Search
CPC ................................ C07C 41/36; Y02A 40/81
See application file for complete search history.

(56) References Cited

U.S. PATENT DOCUMENTS

| | | | |
|---|---|---|---|
| 4,390,468 A | * | 6/1983 | Sasaki .................. C07K 14/435 |
| | | | 530/416 |
| 2016/0200653 A1 | | 7/2016 | Watanabe et al. |

FOREIGN PATENT DOCUMENTS

| | | | |
|---|---|---|---|
| JP | H07285874 | * | 10/1995 |
| JP | 2010-193756 | | 9/2010 |
| WO | 2016/027295 | | 2/2016 |

OTHER PUBLICATIONS

Wright et al. ("Nutritional Value and Food Safety of Bivalve Molluscan Shellfish", Journal of Shellfish Research, vol. 37, No. 4, Oct. 2018, pp. 695-708) (Year: 2018).*
Yon-Suk Kim et al., "Antioxidant and Protective Effects of Atrina Pectinata Extract", Advances in Experimental Medicine and Biology, vol. 1155, pp. 627-641 (2019).
My Korean Kitchen, "Korean Spicy Mussel Stew (Honghap Jiim)" (2019), mykoreankitchen.com, available at https://mykoreankitchen.com/spicy-mussel-stew-honghap-jjim-in-korean/ [Accessed Jun. 14, 2022].
Key Ingredient, "Low Country Boil", keyingrediennt.com, available at https://www.keyingredient.com/recipes/3543655032/low-country-boil/ [Accessed Jun. 14, 2022].
J. J. Waterman, "Processing Mussels, Cockles and Whelks," (2001), fao.org, available at https://www.fao.org/3/x5894e/x5894e00.htm [Accessed Jun. 14, 2022].
International Search Report (ISR) issued Nov. 26, 2019 in International (PCT) Application No. PCT/JP2019/038301.
Peter A. Plack et al., "Gadusol, an enolic derivative of cyclohexane-1,3-dione present in the roes of cod and other marine fish", Biochemical Journal, vol. 199, No. 3, pp. 741-747, 1981.
Patrick T. Grant et al., "Gadusol, A Metabolite From Fish Eggs", Tetrahedron Letters, vol. 21, No. 41, pp. 4043-4044.
Zhe Fang et al., "Anticholinesterase and Antioxidant Constituents from *Gloiopeltis furcata*", Chemical & Pharmaceutical Bulletin, vol. 58, No. 9, pp. 1236-1239, 2010.
Mitsugu Watanabe et al., "Isolation and Characterization of a Phenolic Antioxidant from the Pacific Oyster (*Crassostrea gigas*)", Journal of Agricultural and Food Chemistry, 2012, vol. 60, pp. 830-835.

* cited by examiner

*Primary Examiner* — Sikarl A Witherspoon
(74) *Attorney, Agent, or Firm* — Wenderoth, Lind & Ponack, L.L.P.

(57) ABSTRACT

The purpose of the present invention is to enable the production of 3,5-dihydroxy-4-methoxybenzyl alcohol (DHMBA), which is a novel antioxidant, from the shellfish meat of a filter-feeding bivalve other than oyster by extracting the shellfish meat of the filter-feeding bivalve under heating or pressurizing. The method according to the present invention is characterized by comprising adding the shellfish meat of a filter-feeding bivalve other than oyster to an extraction liquid and heating the extraction liquid to thereby produce 3,5-dihydroxy-4-methoxybenzyl alcohol from the thus heated shellfish meat liquid of the bivalve.

11 Claims, 3 Drawing Sheets

Fig.1

RESULTS OF BIVALVE DHMBA EXTRACTION TEST (HEATING)

| SPECIES | CULTIVATION AREA | DHMBA CONCENTRATION IN BIVALVE SOFT BODY TISSUE (ng/g) | | | | |
|---|---|---|---|---|---|---|
| | | 1 HOUR | 2 HOURS | 3 HOURS | 4 HOURS | 5 HOURS |
| ATRINA PECTINATA | AICHI | 389.5 | 758.3 | 1127.6 | 1660.7 | 2186.3 |
| MEGANGULUS VENULOSUS | HOKKAIDO | 174.4 | 368.0 | 645.4 | 928.0 | 1233.3 |
| ANADARA BROUGHTONII | OITA | 0.0 | 0.0 | 0.0 | 0.0 | 61.4 |
| MYTILUS CORUSCUS | MIYAGI | 0.0 | 0.0 | 0.0 | 0.0 | 122.6 |
| PATINOPECTEN YESSOENSIS | MIYAGI | 0.0 | 75.4 | 148.7 | 257.8 | 393.3 |

Fig.2

RESULTS OF BIVALVE DHMBA EXTRACTION TEST (PRESSURIZATION)

| SPECIES | CULTIVATION AREA | DHMBA CONCENTRATION IN BIVALVE SOFT BODY TISSUE (ng/g) | | | | |
|---|---|---|---|---|---|---|
| | | 1 HOUR | 2 HOURS | 3 HOURS | 4 HOURS | 5 HOURS |
| ATRINA PECTINATE | AICHI | 735.9 | 1711.7 | 2774.7 | 5163.8 | 7073.4 |
| MEGANGULUS VENULOSUS | HOKKAIDO | 1063.3 | 1502.4 | 2276.7 | 2190.3 | 3809.5 |
| ANADARA BROUGHTONII | OITA | 0.0 | 0.0 | 131.9 | 234.2 | 416.7 |
| PSEUDOCARDIUM SACHALINENSE | HOKKAIDO | 0.0 | 0.0 | 228.4 | 0.0 | 175.8 |
| MERETRIX LUSORIA | CHIBA | 0.0 | 0.0 | 0.0 | 109.9 | 236.0 |
| MYTILUS CORUSCUS | MIYAGI | 0.0 | 0.0 | 268.3 | 390.2 | 742.0 |
| PATINOPECTEN YESSOENSIS | MIYAGI | 169.7 | 237.4 | 387.7 | 436.6 | 731.4 |

METHOD FOR PRODUCING 3,5-DIHYDROXY-4-METHOXYBENZYL ALCOHOL FROM BIVALVE

TECHNICAL FIELD

The present invention relates to a method for extracting and producing 3,5-dihydroxy-4-methoxybenzyl alcohol (hereinafter referred to as DHMBA) as an antioxidant from a shellfish meat of, what is called, a filter-feeding bivalve, in particular, a method for extracting and producing DHMBA from the shellfish meat of the filter-feeding bivalve other than an oyster.

BACKGROUND ART

An oyster, for example, *Crassostrea gigas* is a bivalve belonging to Pterioida Ostreidae, and its habitat extends to the whole region of East Asia, including Japan. In recent years, *Crassostrea gigas* is cultivated also in France and Australia and is famous as the oyster most used for food in the world.

The oyster has been used for food from ancient times because it has high nutritive values and, as described above, in addition to glycogen and proteins, contains a large amount of minerals such as calcium, zinc, selenium, copper, and manganese.

As reported oyster-derived antioxidants, included were SOD, CAT, GPx, and Prx6 as an enzymatic antioxidant and metallothionein, uncouplingprotein5 (UCP5), ascorbic acid, α-tocopherol, and β-carotene as a non-enzymatic antioxidant.

CITATION LIST

Patent Literature

Patent Document 1: JP-A-2010-19375

DISCLOSURE OF THE INVENTION

Problems to be Solved by the Invention

In recent years, the inventor of the present invention has succeeded in finding out an excellent novel antioxidant from an oyster, DHMBA and, in addition, has succeeded in determining its chemical structure and also performing chemical synthesis of the antioxidant and, furthermore, has succeeded in enabling to provide a novel antioxidant agent and an antioxidant agent composition containing excellent, what is called, DHMBA as an active ingredient in both the cases where DHMBA is not derived from the oyster or is derived from the oyster.

Further, the inventor of the present invention has succeeded in extracting and producing DHMBA from shellfish meats of filter-feeding bivalves other than the oyster, for example, *Mytilus coruscus, Atrina pectinata, Megangulus venulosus, Anadara broughtonii*, and *Patinopecten yessoensis*.

Solutions to the Problems

The present invention includes: putting a shellfish meat of a bivalve other than an oyster into an extraction liquid; and heating the extraction liquid to produce 3,5-dihydroxy-4-methoxybenzyl alcohol from a shellfish meat liquid of the bivalve. The shellfish meat liquid has been subjected to the heating process.

Alternatively, the present invention includes heating a shellfish meat of a bivalve other than an oyster for 1 hour or more at equal to or more than 95° C. to produce 3,5-dihydroxy-4-methoxybenzyl alcohol from a shellfish meat liquid of the bivalve except an oyster meat. The shellfish meat liquid has been subjected to the heating process.

Alternatively, the present invention includes: extracting a shellfish meat extract by putting a shellfish meat of a bivalve other than an oyster into an extraction solution; heating the extracted shellfish meat extraction liquid; separating a supernatant by centrifuging the heated extraction liquid; and producing 3,5-dihydroxy-4-methoxybenzyl alcohol from the separated supernatant.

Alternatively, in the present invention, the bivalve other than the oyster is *Atrina pectinata, Megangulus venulosus, Anadara broughtonii, Mytilus coruscus*, or *Patinopecten yessoensis*.

Alternatively, the present invention includes: putting a shellfish meat of a bivalve other than an oyster into an extraction liquid; and pressurizing the extraction liquid to produce 3,5-dihydroxy-4-methoxybenzyl alcohol from a shellfish meat liquid of the bivalve. The shellfish meat liquid has been subjected to the pressurization process.

Alternatively, in the present invention, the pressurization is at least equal to or more than 1 atmosphere.

Alternatively, the present invention includes pressurizing a shellfish meat of a bivalve other than an oyster to 2 atmospheres to produce 3,5-dihydroxy-4-methoxybenzyl alcohol from a shellfish meat liquid of the bivalve other than an oyster meat. The shellfish meat liquid has been subjected to the pressurization process.

Alternatively, the present invention includes: putting a shellfish meat of a bivalve other than an oyster into an extraction solution; extracting a shellfish meat extract; pressurizing the extracted shellfish meat extraction liquid; and centrifuging the pressurized extraction liquid to separate a supernatant to produce 3,5-dihydroxy-4-methoxybenzyl alcohol from the separated supernatant.

Alternatively, in the present invention, the bivalve other than the oyster is *Atrina pectinata, Megangulus venulosus, Anadara broughtonii, Pseudocardium sachalinense, Meretrix lusoria, Mytilus coruscus*, or *Patinopecten yessoensis*.

Effects of the Invention

According to the present invention, an excellent effect that allows to extract and produce DHMBA, which is the novel antioxidant, from the shellfish meat of the filter-feeding bivalve other than the oyster, by heating or pressurizing the shellfish meat of the filter-feeding bivalve is achieved.

BRIEF DESCRIPTION OF THE DRAWINGS

FIG. 1 is an explanatory view illustrating a detection result of DHMBA detected from a bivalve other than an oyster by heating.

FIG. 2 is a graph illustrating a detection result of DHMBA detected from the bivalve other than the oyster by pressurization.

DESCRIPTION OF PREFERRED EMBODIMENTS

Figure 3:
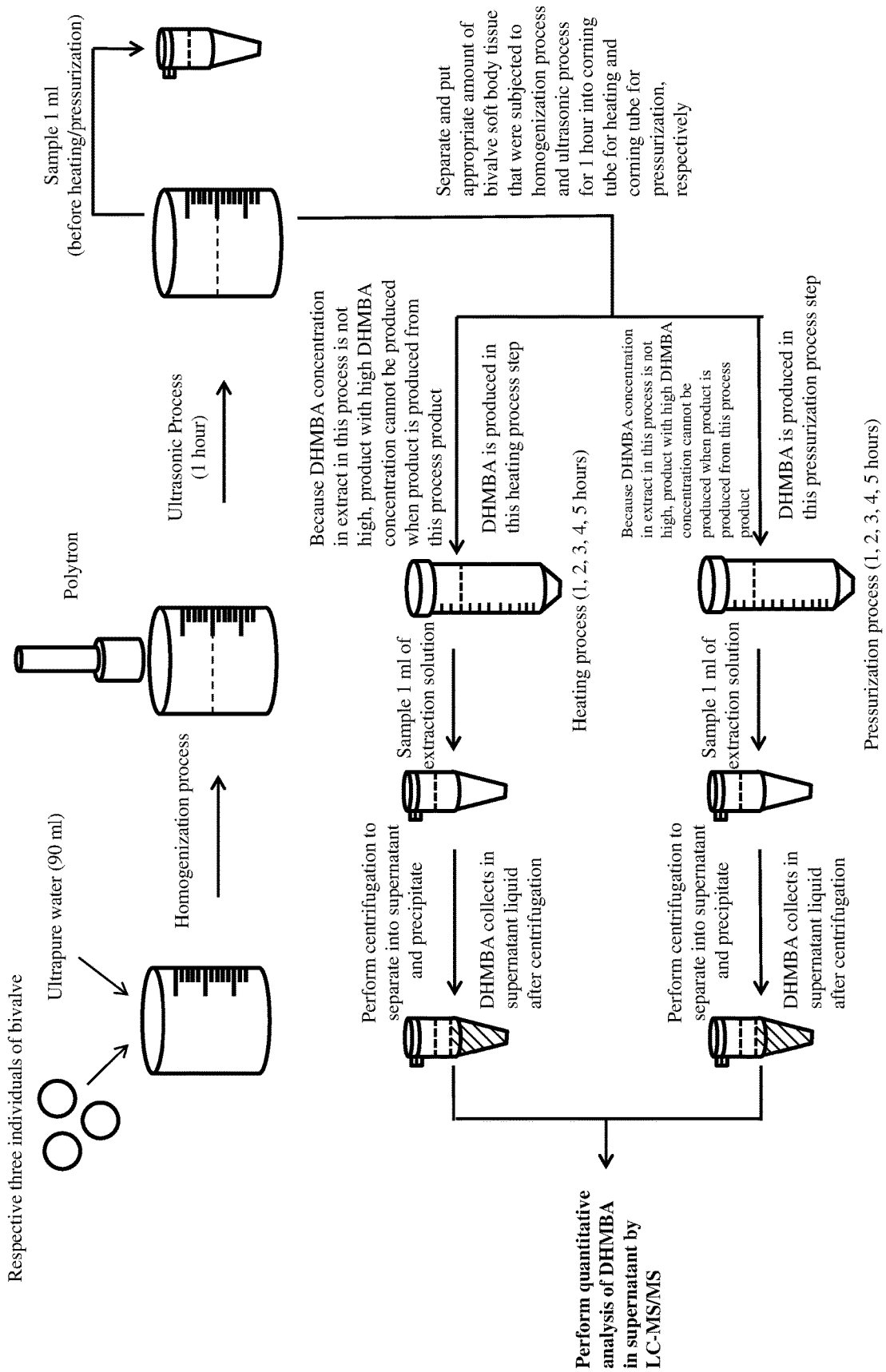
FIG. 3 is an explanatory view describing a configuration of the present invention.

The following describes the present invention based on one working example illustrated in the views.

(Extraction of DHMBA by Heating)

First, a large number of filter-feeding bivalves other than an oyster was prepared. Then, among the large number of filter-feeding bivalves, predetermined species of bivalves were selected, and, among them, respective three individuals were randomly selected.

The selected bivalve species related to the three individuals were *Atrina pectinata, Megangulus venulosus, Anadara broughtonii, Mytilus coruscus*, and *Patinopecten yessoensis*.

Then, from each of *Atrina pectinata, Megangulus venulosus, Anadara broughtonii, Mytilus coruscuss*, and *Patinopecten yessoensis*, shellfish meats, namely, soft body tissues of them were extracted to perform weight measurement.

The extracted soft body tissue of the three individuals was put into different storage tools (beakers), respectively, and, after ultrapure water or pure water was added by approximately 90 mL into the storage tool, a homogenization process was performed.

Here, the homogenization process means pulverizing or grinding the tissue of the shellfish meat or the like to make it a uniform suspended state. In the homogenization process, Polytron PT10-35 produced by Kinematica AG was used.

Subsequently, the appropriate amount of soft body tissue of the shellfish meat, which had turned into a liquid state by the homogenization process, was put into a 50 mL corning tube (AS ONE Corporation), and the weight measurement was performed again.

Further, to improve an extraction state of the antioxidant to be extracted, DHMBA by breaking a cell membrane of the bivalve soft body tissue where the homogenization process was performed, an ultrasonic process was performed for about 1 hour using a corning tube, for example, an ultrasonic cleaning machine (ASU-10 made by AS ONE Corporation).

Then, after a lapse of about 1 hour, 1 mL of sample was sampled from each corning tube and stored in a 1.5 mL Eppendorf tube.

Next, each corning tube was put into hot water of about 100° C., in other words, heated at equal to or more than 95° C. using a IH heater (KZ-PH3 made by National) to perform a thermal extraction (hot water extraction) of the antioxidant, DHMBA. The thermal extraction is not limited to the hot water extraction.

Here, the heating of total 5 hours was performed. A sampling was performed five times every 1 hour. At the sampling, 1 mL of sample was sampled from each corning tube and stored in the 1.5 mL Eppendorf tube, and these were performed for Time=1 to 5 (T=1 hour to 5 hours).

Then, a centrifugal separation process was performed for each Eppendorf tube where the sampling was performed to separate a supernatant and a precipitate. Then, the centrifuged supernatant was stored in a different Eppendorf tube.

A concentration of the antioxidant, DHMBA in the supernatant, which was stored in the different Eppendorf tube, after the centrifugal separation was measured. The measurement was performed by a quantitative determination using a liquid chromatogram/tandem mass spectrometer (LC-MS/MS: Prominence high-pressure gradient HPLC, triple quadrupole mass meter LCMS-8040 system, Shimadzu Corporation).

Here, a standard product (made by Ushio Chemix Corporation) of the antioxidant, DHMBA was dissolved in pure water to prepare 0.5 ng/mL, 1.5 ng/mL, 10 ng/mL, and 50 ng/mL of calibration curve solution.

Each sample was diluted 100 times and subjected to a quantitative analysis by LC-MS/MS. For a separation column, Shim-Pack VP-ODS (length 150 mm×inner diameter 2.0 mm, particle size 5 μm), which is an ODS, was used. By using a mobile phase A: 0.05% acetic acid aqueous solution and a mobile phase B: acetonitrile, a gradient analysis (the mobile phase B: 0 min 5%→5 min 100%→7.5 min 5%→12 min 5%) was performed. A flow rate was set to 0.25 mL/min, and a column oven temperature was set to 40° C.

A sample injection amount was set to 1 μL, and the antioxidant, DHMBA was detected in a negative ion mode. For the quantitative analysis, a product ion scan was used. In the product ion scan, m/z 169.1, which is a deprotonated ion [M-H]- of DHMBA, was set as a precursor ion, and the analysis was performed at 10 V, 20 V, and 30 V.

In the quantitative analysis, an Electrospray Ionization method (ESI method) was used for an ionization method, and a Multiple Reaction Monitoring (MRM) was used. An MRM transition was determined by automatic optimization. Q1/Q3=169.1/154.1 (a transition for quantitative determination), 169.1/136.9, and 169.1/125.1 (a transition for qualitative determination) were used. Respective Collision energies were set to 15 V, 28 V, and 13 V. In addition, as parameters of MS, a DL temperature was set to 250° C., a flow rate of a nebulizer gas was set to 3 L/min, a heat block temperature was set to 400° C., and a dry-in gas flow rate was set to 15 L/min.

With the above-described operations, the detection results indicated in FIG. 1 were obtained.

For *Atrina pectinata*, after the lapse of 1 hour after the heating, 389.5 (ng/g) of DHMBA was obtained. After the lapse of 2 hours after the heating, 758.3 (ng/g) of DHMBA was obtained, and after the lapse of 3 hours after the heating, 1127.6 (ng/g) of DHMBA was obtained. Furthermore, it was confirmed that, after the lapse of 4 hours after the heating, 1660.7 (ng/g) of DHMBA was obtained, and, after the lapse of 5 hours after the heating, 2186.3 (ng/g) of DHMBA was obtained.

For the *Megangulus venulosus*, after the lapse of 1 hour after the heating, 174.4 (ng/g) of DHMBA was obtained. After the lapse of 2 hours after the heating, 368.0 (ng/g) of DHMBA was obtained, and after the lapse of 3 hours after the heating, 645.4 (ng/g) of DHMBA was obtained. Furthermore, after the lapse of 4 hours after the heating, 928.0 (ng/g) of DHMBA was obtained, and, after the lapse of 5 hours after the heating, 1233.3 (ng/g) of DHMBA was obtained.

Further, for *Anadara broughtonii*, while during 1 to 4 hours after the heating, DHMBA was not obtained, after the lapse of 5 hours after the heating, 61.4 (ng/g) of DHMBA was obtained.

For *Mytilus coruscus*, while during 1 to 4 hours after the heating, DHMBA was not obtained, after the lapse of 5 hours after the heating, 122.6 (ng/g) of DHMBA was obtained.

For *Patinopecten yessoensis*, while after the lapse of 1 hour after the heating, DHMBA was not obtained, after the lapse of 2 hours after the heating, 75.4 (ng/g) of DHMBA was obtained, and, after the lapse of 3 hours after the heating, 148.7 (ng/g) of DHMBA was obtained. Furthermore, after the lapse of 4 hours after the heating, 257.8 (ng/g) of DHMBA was obtained, and, after the lapse of 5 hours after the heating, 393.3 (ng/g) of DHMBA was obtained.

As described above, DHMBA as the antioxidant was also able to be extracted and produced from the shellfish meat of the filter-feeding bivalve other than the oyster by heating the shellfish meat of the filter-feeding bivalve.

(Extraction of DHMBA by Pressurization)

First, a large number of filter-feeding bivalves other than the oyster was prepared. Then, among the large number of filter-feeding bivalves, predetermined species of bivalves were selected, and, among them, respective three individuals were randomly selected.

The selected bivalve species related to the three individuals were *Atrina pectinata, Megangulus venulosus, Anadara broughtonii, Pseudocardium sachalinense, Meretrix lusoria, Mytilus coruscus*, and *Patinopecten yessoensis*.

Then, from each of *Atrina pectinata, Megangulus venulosus, Anadara broughtonii, Pseudocardium sachalinense, Meretrix lusoria, Mytilus coruscus*, and *Patinopecten yessoensis*, the shellfish meat, namely, the soft body tissue of them was extracted to perform weight measurement.

The extracted soft body tissue of the three individuals was put into different storage tools (beakers), respectively, and, after ultrapure water or pure water was added by approximately 90 mL into the storage tool, a homogenization process was performed. Here, the homogenization process assumes pulverizing or grinding the tissue of the shellfish meat or the like to make it a uniform suspended state as an index.

In the homogenization process, Polytron PT10-35 produced by Kinematica AG was used. Subsequently, the appropriate amount of soft body tissue of the shellfish meat, which had become a liquid state by the homogenization process, was put into the 50 mL corning tube (AS ONE Corporation), and the weight measurement was performed again.

Further, to improve an extraction state of the antioxidant to be extracted, DHMBA by breaking a cell membrane of the bivalve soft body tissue where the homogenization process was performed, the ultrasonic process was performed for about 1 hour using the corning tube, for example, the ultrasonic cleaning machine (ASU-10 made by AS ONE Corporation).

Then, after the lapse of about 1 hour, 1 mL of sample was sampled from each corning tube and stored in the 1.5 mL Eppendorf tube.

Next, the sample was extracted by pressurizing to a pressure of 2 atmospheres. While the present inventor performed an extraction operation of DHMBA by pressurizing to a pressure of 2 atmospheres, it is not limited to the pressurization to a pressure of 2 atmospheres, and it is only necessary to pressurize to a pressure of equal to or more than 1 atmosphere for the extraction of DHMBA.

The pressurization method is also not limited. Pressurization may be performed using an autoclave, which is a typical method. Furthermore, Pressurization may be performed by other methods.

Here, the pressurization of total 5 hours was performed. The sampling was performed five times every 1 hour. At the sampling, 1 mL of sample was sampled from each corning tube and stored in 1.5 mL Eppendorf tube, and these were performed for Time=1 to 5 (T=1 hour to 5 hours).

Then, the centrifugal separation process was performed for each Eppendorf tube where the sampling was performed, and the centrifuged supernatant was stored in a different Eppendorf tube.

Then, the concentration of the antioxidant, DHMBA in the supernatant, which was stored in the different Eppendorf tube, after the centrifugal separation was measured. The concentration was quantitatively determined using the liquid chromatogram/tandem mass spectrometer (LC-MS/MS: Prominence high-pressure gradient HPLC, triple quadrupole mass meter LCMS-8040 system, Shimadzu Corporation).

Here, the standard product (made by Ushio Chemix) of the antioxidant, DHMBA was dissolved in pure water to prepare 0.5 ng/mL, 1 ng/mL, 5 ng/mL, 10 ng/mL, and 50 ng/mL of calibration curve solution.

Each sample was diluted 100 times and subjected to the quantitative analysis by LC-MS/MS. For the separation column, Shim-Pack VP-ODS (length 150 mm×inner diameter 2.0 mm, particle size 5 μm), which is the ODS, was used. By using the mobile phase A: 0.05% acetic acid aqueous solution and the mobile phase B: acetonitrile, the gradient analysis (the mobile phase B: 0 min 5%→5 min 100%→7.5 min 5%→12 min 5%) was performed. The flow rate was set to 0.25 mL/min, and the column oven temperature was set to 40° C.

The sample injection amount was set to 1 μL, and the antioxidant, DHMBA was detected in the negative ion mode. For the quantitative analysis, the product ion scan was used. In the product ion scan, m/z 169.1, which is the deprotonated ion [M-H]– of DHMBA, was set as the precursor ion, and the analysis was performed at 10 V, 20 V, and 30 V.

In the quantitative analysis, the Electrospray Ionization method (ESI method) was used for the ionization method, and the Multiple Reaction Monitoring (MRM) was used. The MRM transition was determined by automatic optimization. Q1/Q3=169.1/154.1 (the transition for a quantitative determination), 169.1/136.9, and 169.1/125.1 (the transition for qualitative determination) were used. The respective Collision energies were set to 15 V, 28 V, and 13 V. In addition, as parameters of MS, the DL temperature is set to 250° C., the flow rate of the nebulizer gas was set to 3 L/min, the heat block temperature was set to 400° C., and the dry-in gas flow rate was set to 15 L/min.

With the above-described operations, the detection results indicated in FIG. 2 were obtained.

For *Atrina pectinata*, after the lapse of 1 hour after the pressurization, 735.9 (ng/g) of DHMBA was obtained. After the lapse of 2 hours after the pressurization, 1711.7 (ng/g) of DHMBA was obtained, and after the lapse of 3 hours after the pressurization, 2774.7 (ng/g) of DHMBA was obtained. Furthermore, it was confirmed that, after the lapse of 4 hours after the pressurization, 5163.8 (ng/g) of DHMBA was obtained, and, after the lapse of 5 hours after the pressurization, 7073.4 (ng/g) of DHMBA was obtained.

For *Megangulus venulosus*, after the lapse of 1 hour after the pressurization, 1063.3 (ng/g) of DHMBA was obtained. After the lapse of 2 hours after the pressurization, 1502.4 (ng/g) of DHMBA was obtained, and after the lapse of 3 hours after the pressurization, 2276.7 (ng/g) of DHMBA was obtained. Furthermore, after the lapse of 4 hours after the pressurization, 2190.3 (ng/g) of DHMBA was obtained, and, after the lapse of 5 hours after the pressurization, 3809.5 (ng/g) of DHMBA was obtained.

For *Anadara broughtonii*, while during 1 hour to 2 hours after the pressurization, DHMBA was not obtained, after the lapse of 3 hours after the pressurization, 131.9 (ng/g) of DHMBA was obtained. Furthermore, after the lapse of 4 hours after the pressurization, 234.2 (ng/g) of DHMBA was obtained, and, after the lapse of 5 hours after the pressurization, 416.7 (ng/g) of DHMBA was obtained.

For *Pseudocardium sachalinense* also, while during 1 hour to 2 hours after the pressurization, DHMBA was not obtained, after the lapse of 3 hours after the pressurization, 228.4 (ng/g) of DHMBA was obtained. Furthermore, after the lapse of 5 hours after the pressurization, 175.8 (ng/g) of DHMBA was obtained.

For *Meretrix lusoria*, while during 1 hour to 3 hours after the pressurization, DHMBA was not obtained, after the lapse of 4 hours after the pressurization, 109.9 (ng/g) of DHMBA was obtained. Furthermore, after the lapse of 5 hours after the pressurization, 236.0 (ng/g) of DHMBA was obtained.

For *Mytilus coruscus*, while during 1 hour to 2 hours after the pressurization, DHMBA was not obtained, after the lapse of 3 hours after the pressurization, 268.3 (ng/g) of DHMBA was obtained. Then, after the lapse of 4 hours after the pressurization, 390.2 (ng/g) of DHMBA was obtained. Furthermore, after the lapse of 5 hours after the pressurization, 742.0 (ng/g) of DHMBA was obtained.

For *Patinopecten yessoensis*, after the lapse of 1 hour after the pressurization, 169.7 (ng/g) of DHMBA was obtained, after the lapse of 2 hours after the pressurization, 237.4 (ng/g) of DHMBA was obtained, and after the lapse of 3 hours after the pressurization, 387.7 (ng/g) of DHMBA was obtained. Furthermore, after the lapse of 4 hours after the pressurization, 436.6 (ng/g) of DHMBA was obtained, and, after the lapse of 5 hours after the pressurization, 731.4 (ng/g) of DHMBA was obtained.

As described above, DHMBA as the antioxidant was able to be extracted and produced also from the shellfish meat of the filter-feeding bivalve other than the oyster by pressurizing the shellfish meat of the filter-feeding bivalve.

The invention claimed is:

1. A method for producing 3,5-dihydroxy-4-methoxybenzyl alcohol from a shellfish meat of Megangulus venulosus, the method comprising:
    putting the shellfish meat into an extraction liquid;
    heating the extraction liquid at a temperature of at least 95° C. for at least 1 hour to produce 3,5-dihydroxy-4-methoxybenzyl alcohol;
    separating and isolating the 3,5-dihydroxy-4-methoxybenzyl alcohol from the heated extraction liquid; and
    measuring a concentration of the separated and isolated 3,5-dihydroxy-4-methoxybenzyl alcohol to obtain at least 174.4 ng/g of the separated and isolated 3,5-dihydroxy-4-methoxybenzyl alcohol.

2. The method for producing 3,5-dihydroxy-4-methoxybenzyl alcohol from the shellfish meat of Megangulus venulosus according to claim 1, further comprising:
    performing an ultrasonic process of the extraction liquid before the heating;
    then heating the extraction liquid at a temperature of at least 95° C. for at least 1 hour to produce the 3,5-dihydroxy-4-methoxybenzyl alcohol;
    separating and isolating a supernatant comprising the 3,5-dihydroxy-4-methoxybenzyl alcohol by centrifuging the heated extraction liquid; and
    measuring the concentration of the 3,5-dihydroxy-4-methoxybenzyl alcohol in the separated and isolated supernatant to obtain the at least 174.4 ng/g of the separated and isolated 3,5-dihydroxy-4-methoxybenzyl alcohol.

3. A method for producing 3,5-dihydroxy-4-methoxybenzyl alcohol from a shellfish meat of Megangulus venulosus or Patinopecten yessoensis, the method comprising:
    putting the shellfish meat of Megangulus venulosus or Patinopecten yessoensis into an extraction liquid;
    pressurizing the extraction liquid for at least 1 hour to produce 3,5-dihydroxy-4-methoxybenzyl alcohol;
    separating and isolating the 3,5-dihydroxy-4-methoxybenzyl alcohol from the pressurized extraction liquid; and
    measuring a concentration of the separated and isolated 3,5-dihydroxy-4-methoxybenzyl alcohol to obtain at least 1063.3 ng/g of the separated and isolated 3,5-dihydroxy-4-methoxybenzyl alcohol from the shellfish meat of Megangulus venulosus or at least 169.7 ng/g from the shellfish meat of Patinopecten yessoensis.

4. The method for producing 3,5-dihydroxy-4-methoxybenzyl alcohol from the shellfish meat of Megangulus venulosus or Patinopecten yessoensis according to claim 3, wherein
    the pressurizing is at least equal to or more than 1 atmosphere.

5. The method for producing 3,5-dihydroxy-4-methoxybenzyl alcohol from a shellfish meat of Megangulus venulosus or Patinopecten yessoensis according to claim 4,
    wherein the pressurizing is at 2 atmospheres.

6. The method for producing 3,5-dihydroxy-4-methoxybenzyl alcohol from the shellfish meat of Megangulus venulosus or Patinopecten yessoensis according to claim 3, further comprising:
    performing an ultrasonic process of the extraction liquid before the pressurizing;
    then pressurizing the extraction liquid to produce the 3,5-dihydroxy-4-methoxybenzyl alcohol;
    centrifuging the pressurized extraction liquid to separate and isolate a supernatant comprising the 3,5-dihydroxy-4-methoxybenzyl alcohol from the pressurized extraction liquid; and
    measuring the concentration of the 3,5-dihydroxy-4-methoxybenzyl alcohol in the separated and isolated supernatant to obtain the at least 1063.3 ng/g of the separated and isolated 3,5-dihydroxy-4-methoxybenzyl alcohol from the shellfish meat of Megangulus venulosus or the at least 169.7 ng/g from the shellfish meat of *Patinopecten yessoensi*.

7. The method for producing 3,5-dihydroxy-4-methoxybenzyl alcohol from the shellfish meat of Megangulus venulosus or Patinopecten yessoensis according to claim 4, further comprising:
    performing an ultrasonic process of the extraction liquid before the pressurizing;
    then pressurizing the extraction liquid to produce the 3,5-dihydroxy-4-methoxybenzyl alcohol;
    centrifuging the pressurized extraction liquid to separate and isolate a supernatant comprising the 3,5-dihydroxy-4-methoxybenzyl alcohol from the pressurized extraction liquid; and
    measuring the concentration of the 3,5-dihydroxy-4-methoxybenzyl alcohol in the separated and isolated supernatant to obtain the at least 1063.3 ng/g of the separated and isolated 3,5-dihydroxy-4-methoxybenzyl alcohol from the shellfish meat of Megangulus venulosus or the at least 169.7 ng/g from the shellfish meat of Patinopecten yessoensi.

8. A method for producing 3,5-dihydroxy-4-methoxybenzyl alcohol from a shellfish meat of Anadara broughtonii or Mytilus coruscus, the method comprising:
    putting the shellfish meat into an extraction liquid;
    heating the extraction liquid at a temperature of at least 95° C. for at least 5 hours to produce 3,5-dihydroxy-4-methoxybenzyl alcohol;
    separating and isolating the 3,5-dihydroxy-4-methoxybenzyl alcohol from the heated extraction liquid; and
    measuring a concentration of the separated and isolated 3,5-dihydroxy-4-methoxybenzyl alcohol to obtain at least 61.4 ng/g of the separated and isolated 3,5-dihydroxy-4-methoxybenzyl alcohol from the shellfish meat of Anadara broughtonii or at least 122.6 ng/g from the shellfish meat of Mytilus coruscus.

9. A method for producing 3,5-dihydroxy-4-methoxybenzyl alcohol from a shellfish meat of Patinopecten yessoensis, the method comprising:
putting the shellfish meat into an extraction liquid;
heating the extraction liquid at a temperature of at least 95° C. for at least 2 hours to produce 3,5-dihydroxy-4-methoxybenzyl alcohol;
separating and isolating the 3,5-dihydroxy-4-methoxybenzyl alcohol from the heated extraction liquid; and
measuring a concentration of the separated and isolated 3,5-dihydroxy-4-methoxybenzyl alcohol to obtain at least 75.4 ng/g of the separated and isolated 3,5-dihydroxy-4-methoxybenzyl alcohol.

10. A method for producing 3,5-dihydroxy-4-methoxybenzyl alcohol from a shellfish meat of Anadara broughtonii, Pseudocardium *sachalinense* or Mytilus coruscus, the method comprising:
putting the shellfish meat into an extraction liquid;
pressurizing the extraction liquid for at least 3 hours to produce 3,5-dihydroxy-4-methoxybenzyl alcohol;
separating and isolating the 3,5-dihydroxy-4-methoxybenzyl alcohol from the pressurized extraction liquid; and
measuring a concentration of the separated and isolated 3,5-dihydroxy-4-methoxybenzyl alcohol to obtain at least 131.9 ng/g of the separated and isolated 3,5-dihydroxy-4-methoxybenzyl alcohol from the shellfish meat of Anadara broughtonii, at least 228.4 ng/g of the separated and isolated 3,5-dihydroxy-4-methoxybenzyl alcohol from the shellfish meat of *Pseudocardium sachalinense* or at least 268.3 ng/g of the separated and isolated 3,5-dihydroxy-4-methoxybenzyl alcohol from the shellfish meat of Mytilus coruscus.

11. A method for producing 3,5-dihydroxy-4-methoxybenzyl alcohol from a shellfish meat of Meretrix lusoria, the method comprising:
putting the shellfish meat into an extraction liquid;
pressurizing the extraction liquid for at least 4 hours to produce 3,5-dihydroxy-4-methoxybenzyl alcohol;
separating and isolating the 3,5-dihydroxy-4-methoxybenzyl alcohol from the pressurized extraction liquid; and
measuring a concentration of the separated and isolated 3,5-dihydroxy-4-methoxybenzyl alcohol to obtain at least 109.9 ng/g of the separated and isolated 3,5-dihydroxy-4-methoxybenzyl alcohol from the shellfish meat of Meretrix lusoria.

\* \* \* \* \*